United States Patent [19]

Tang

[11] Patent Number: 5,231,211
[45] Date of Patent: Jul. 27, 1993

[54] METHOD FOR PREPARING DI(ORGANO) ESTERS OF PYROCARBONIC ACID

[75] Inventor: Robert H. Tang, Murrysville, Pa.

[73] Assignee: PPG Industries, Inc., Pittsburgh, Pa.

[21] Appl. No.: 947,211

[22] Filed: Sep. 18, 1992

[51] Int. Cl.$^5$ ............................................. C07C 69/96
[52] U.S. Cl. ................................... 558/276; 558/260; 558/270; 558/274; 558/277
[58] Field of Search ............... 558/260, 270, 274, 276, 558/277

[56] References Cited

U.S. PATENT DOCUMENTS

| | | | |
|---|---|---|---|
| 3,326,958 | 12/1992 | Curtius | 558/276 |
| 4,929,748 | 12/1992 | Franklin | 558/276 |
| 5,142,086 | 8/1992 | King, Jr. et al. | 558/276 |

*Primary Examiner*—Johann Richter
*Attorney, Agent, or Firm*—Irwin M. Stein

[57] ABSTRACT

Di(organo) esters of pyrocarbonic acid, e.g., dialkyl pyrocarbonates, such as diethyl pyrocarbonate, are prepared by reaction of the corresponding organohaloformate with aqueous alkali metal hydroxide, e.g., sodium hydroxide, in the substantial absence of an organic solvent and in the presence of a catalytic amount of a bis[poly(oxy($C_2$–$C_4$)alkylene)] $C_6$–$C_{20}$ aliphatic amine, e.g., coco bis(polyoxyethylene) amine.

20 Claims, No Drawings

METHOD FOR PREPARING DI(ORGANO) ESTERS OF PYROCARBONIC ACID

DESCRIPTION OF THE INVENTION

The present invention relates to a method for preparing di(organo) esters of pyrocarbonic acid, e.g., dialkyl dicarbonates, which are also known as dialkyl pyrocarbonates.

Dialkyl pyrocarbonates have found a variety of uses in synthetic chemistry and in biological applications. These materials, particularly diethyl pyrocarbonate, have been used for the preparation of beta-ketoesters, for the protection of amino groups during peptide synthesis, as fermentation inhibitors in wines, beer and fruit juices, for stabilizing polyurethane-containing polymers against color formation, as blowing agents for polymers and as nuclease inhibitors.

U.S. Pat. No. 3,326,958 describes a process for preparing dialkyl and diphenyl pyrocarbonate. In that process, the corresponding chloroformate, e.g., ethyl chloroformate, is dissolved in an organic solvent such as methylene chloride and reacted with sodium hydroxide in the presence of the ethoxylated or propoxylated secondary amine N-methylstearyl amine as the catalyst. This method suffers from the disadvantages of using a chlorinated organic solvent and in requiring distillation as part of the product recovery procedure. Solvents such as methylene chloride give rise to increased manufacturing costs because of the possible environmental safeguards which must be incorporated into the process to eliminate their emission into the air and their contamination of any aqueous effluent discharged from the process. Further, since many of the common dialkyl and diaryl pyrocarbonates are thermally unstable, the use of distillation procedures in the recovery procedure requires special conditions, e.g., high vacuum and low temperatures, to avoid loss of product. Generally, it is preferable to avoid distillation of the pyrocarbonate products, if at all possible.

U.S. Pat. No. 4,929,748 describes a process of preparing dialkyl dicarbonates by reacting an alkyl haloformate and an alkali metal carbonate in the presence of a crown ether and a suitable organic solvent, e.g., acetonitrile, dichloromethane (methylene chloride), toluene, tetrahydrofuran or N,N-dimethyl formamide. This described process also suffers from the disadvantage of using an organic solvent.

It has now been discovered that di(organo) esters of pyrocarbonic acid, e.g., dialkyl pyrocarbonates, may be prepared by reacting the corresponding organohaloformate with an aqueous solution of alkali metal hydroxide, e.g., sodium hydroxide, in the presence of a catalytic amount of a bis[poly(oxyalkylene)] $C_8$-$C_{18}$ aliphatic amine and in the substantial absence of an organic solvent. The process of the present invention does not suffer from the disadvantage of using an organic solvent, i.e., it is free of organic solvent and hence environmentally friendly, produces high yields of pyrocarbonate product of excellent purity, does not require distillation as part of the product recovery process, and eliminates water insoluble by-products.

DETAILED DESCRIPTION

In accordance with the process of the present invention, di(organo) esters of pyrocarbonic acid are prepared by the reaction of the corresponding organohaloformate or a mixture of organohaloformate with an aqueous solution of alkali metal hydroxide in the presence of the hereinafter described catalyst and in the substantial absence of an organic solvent. The organohaloformate may be represented by the graphic formula,

I wherein R is selected from the group consisting of $C_1$-$C_{12}$ alkyl, $C_6$-$C_{10}$ cycloalkyl and $C_6$-$C_9$ aryl, and X is halogen, i.e., chloro, bromo, or iodo, preferably chloro. More particularly, R is selected from the group consisting of $C_2$-$C_4$ alkyl. Examples of R groups include those such as ethyl, propyl, butyl, secondary butyl, pentyl, hexyl tertiary butyl, 2-ethylhexyl, decyl, dodecyl cyclohexyl, 4-tertiary butyl cyclohexyl, phenyl and methylphenyl. As used in the description and claims, the term "alkyl" when referring to dialkyl pyrocarbonates is intended to means and include both linear and branched chain alkyls; and the term "cycloalkyl" is intended to mean and include both alkyl-substituted and unsubstituted cycloalkyl groups, e.g., cyclohexyl and tertiary butyl cyclohexyl.

The di(organo) esters of pyrocarbonic acid may be represented by the following graphic formula,

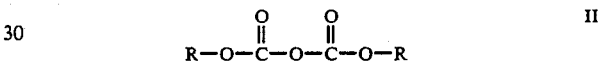
II wherein R is as defined herein with respect to graphic formula I. When mixtures of organohaloformate are sued, e.g., a 50/50 mixture of ethyl chloroformate and isopropyl chloroformate, the resulting product is a statistical mixture of the symmetrical and unsymmetrical dialkyl pyrocarbonates derived from the starting alkyl haloformates, e.g., diethyl pyrocarbonate (25 percent), diisopropyl pyrocarbonate (25 percent) and ethyl isopropyl pyrocarbonate (50 percent). The unsymmetrical mixed pyrocarbonate may be represented by the graphic formula,

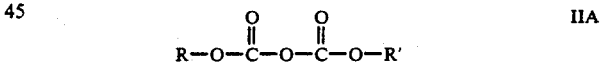
IIA wherein R and R' are each as defined with respect to R in graphic formula II, provided that R is not the same as R'.

The organohaloformate is reacted with an aqueous solution of alkali metal hydroxide, e.g., sodium hydroxide, potassium hydroxide, or lithium hydroxide. Sodium hydroxide is economically preferred. The amount of alkali metal hydroxide used is in about equimolar amounts with the organohaloformate since the alkali metal hydroxide serves as an acid acceptor of the halogen released from the organohaloformate, thereby to form the corresponding alkali metal halide salt, e.g., sodium chloride.

While typically about equimolar amounts of the organohaloformate and alkali metal hydroxide are used, an excess of the organohaloformate may be used to reduce the opportunity for hydrolysis of the organohaloformate. However, an excess of alkali metal hydroxide may also be sued and is particularly contemplated. In the present process, ti si preferred that a slight excess of the alkali metal hydroxide is used. No undue hydrolysis of the organohaloformate has been observed using a slight excess of alkali metal hydroxide in the present process. For example, the mole ratio of alkali metal hydroxide int eh present process. For example, the mole ratio of alkali metal hydroxide to organohaloformate contemplated herein may vary from about 1.0:1 to 1:1.10, e.g., 1.01:1 to 1.08:1.

Suitable examples of dialkyl, diaryl and dicycloalkyl pyrocarbonates include dimethyl pyrocarbonate, diethyl pyrocarbonate, di-isopropyl pyrocarbonate, di-n-propyl pyrocarboante, di-n-butyl pyrocarbonate, di-isobutyl pyrocarboante, di-secondary butyl pyrocarbonate, di-tertiary butyl pyrocarbonate, dipentyl pyrocarbonate, dihexyl pyrocarbonate, diheptyl pyrocarbonate, di-2-ethylhexyl pyrocarboante, dinonyl pyrocarbonate, didecyl pyrocarbonate, di-dodecyl pyrocarbonate, di-cyclohexyl pyrocarboante, di-4-tertiary butyl cyclohexyl pyrocarboante and diphenyl pyrocarbonate. Diethyl pyrocarbonate is economically preferred. As discussed, unsymmetrical diorgano pyrocarbonates are also contemplated, e.g., ethyl isopropyl pyrocarbonate, ethyl secondary butyl pyrocarbonate and ethyl n-propyl pyrocarbonate.

Alkali metal hydroxide aqueous solutions of varying concentrations may be sued in the described process. Contemplated are concentrations of rom about 7 to about 50 weight percent, preferably, from about 35 to about 50 weight percent. It has been found that higher concentrations of alkali metal hydroxide result in higher yields of product.

In accordance with the present invention, a catalytic amount of a bis[poly(oxy($C_4$-$C_4$)alkylene)] $C_6$-$C_{20}$ aliphatic amine is uses as the catalyst for the above-described process. In one embodiment, such amines may be represented by the following graphic formula,

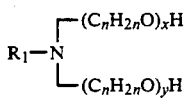   III wherein $R_1$ is a $C_6$-$C_{20}$ alkyl or $C_6$-$C_{20}$ alkenyl, n is an integer of from 2 to 4, and x and y are each average numbers ranging from about 2 to about 24, the sum of x and y being a number of from about 4 to about 48. Preferably, $R_1$ is a $C_8$-$C_{18}$ alkyl, n is the integer 2 or 3, more preferably 2, and x and y are each numbers of from about 2 to 14, the sum of x and y being a number of from 4 to 28, e.g., 5 to 15.

It is also contemplated that the oxyalkylene group may be a block copolymer resulting from the successive alkoxylation of the starting aliphatic primary amine with different $C_2$-$C_4$ alkylene oxides, e.g., a successive ethoxylation and propoxylation of the base amine material. Such amines may be represented, for example, by the graphic formula,

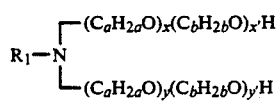   IV wherein $R_1$ is as defined with respect to graphic formula III, a and b are different and are each integers of from 2 to 4, x and y are each numbers averaging from 1 to 24, and x' and y' are each numbers averaging from 0 to 23,
the sum of x, x', y and y' being a number of from about 4 to 48, preferably 4 to 28, e.g., 5 to 15.

Examples of bis[poly(oxyalkylene)] $C_6C_{20}$ aliphatic amine catalysts contemplated include the following compounds. The CTFA adopted name (if known) is also reported.

| COMMON NAME | CTFA NAME |
|---|---|
| polyoxyethylene (5)* cocoamine | PEG-5 cocamine |
| polyoxyethylene (10) cocoamine | PEG-10 cocamine |
| polyoxyethylene (15) cocoamine | PEG-15 cocamine |
| polyoxyethylene (5) octadecylamine | PEG-5 stearamine |
| polyoxyethylene (10) octadecylamine | PEG-10 stearamine |
| polyoxyethylene (15) octadecylamine | PEG-15 stearamine |
| polyoxyethylene (5) tallowamine | PEG-5 tallow amine |
| polyoxyethylene (15) tallowamine | PEG-15 tallow amine |
| polyoxyethylene (5) oleylamine | PEG-5 oleamine |
| polyoxyethylene (15) oleylamine | PEG-15 oleamine |
| polyoxyethylene (5) soyaamine | PEG-5 soyamine |
| polyoxyethylene (10) soyaamine | PEG-10 soyamine |
| polyoxyethylene (15) soyaamine | PEG-15 soyamine |
| polyoxyethylene (5) hexylamine | — |
| polyoxyethylene (5) octylamine | — |
| polyoxyethylene (10) decylamine | — |
| polyoxypropylene (15) cocoamine | — |
| polyoxybutylene (10) octadecylamine | — |
| polyoxypropylene (5) tallowamine | — |
| polyoxybutylene (10) soyaamine | — |

*indicates the average number of oxyalkylene groups in the compound.

Preferably, the catalyst is in liquid form an is light in color, e.g., has a Gardner color of less than 8, preferably 6 or less.

The amount of catalyst used in the above-described reaction is that amount which catalyzes the formation of the di(organo) ester of pyrocarbonic acid, i.e., a catalytic amount. More particularly, the amount of catalyst sued will be from about 0.1 to about 1.0 mole percent, based on the amount of organohaloformate used.

The reaction temperatures that may be sued to prepare the di(organo)esters of pyrocarbonic acid in accordance with the present process will be in the rang of 0° C.-20° C., mqre usually 5° C.-10° C.

In carrying out the process of the present invention, the organohaloformate and catalyst are charged to a suitable cooled reactor, and the aqueous alkali metal hydroxide solution slowly added to the reactor while agitating the reactor contents. After all of the alkali metal hydroxide has been added, and the reaction completed, additional water is added to the reaction flask to achieve a reaction mixture containing a theoretical amount of about 25 to 30 percent solids. The reaction mixture is agitated again to dissolve the solids (salt coproduct) and the mixture allowed to separate into a top organic phase and a bottom aqueous phase.

The aqueous phase is drawn off and the remaining organic phase dried, e.g., over magnesium sulfate. The resultant crude product is purified by removing volatile components remaining therein, e.g., unreacted organohaloformate and any di(organo) carbonate by-product, by, for example, a rotary evaporator.

The present invention is more particularly described in the following examples which are intended as illustrative only, since numerous modifications and variations therein will be apparent to those skilled in the art.

EXAMPLE 1

This example describes the preparation of diethyl pyrocarbonate with PEG 15 stearamine as the catalyst.

A solution of ethyl chloroformate (114.2 grams (95%) 1.00 mole) and PEG-15 stearamine (1.88 grams (99%) 0.002 mole) was introduce to a 1000 milliliter, three-necked reaction flask with a bottom stopcock. The reaction flask was equipped with a mechanical teflon blade stirrer, sodium hydroxide solution inlet, vent and thermowell for a thermocouple, which was connected to a temperature control unit. Sodium hydroxide was charged to the reaction flask through a Masterflex addition pump. The temperature control unit activated a cooling water pump which directed ice water against the reaction flask and also controlled the Masterflex pump so as to maintain the reaction temperature at below 15° C.

When the temperature in the reaction flask was below 15° C., sodium hydroxide solution was charged to the flask. When the temperature rose above 15° C., the Masterflex pump was shut off and ice water sprayed on the reaction flask to cool the contents of the reaction flask.

Aqueous sodium hydroxide solution (82 grams (50%) 1.025 moles) was charged to the reaction flask over a period of approximately 60 minutes. Semi-solids which remained on the sides of the flask were rinsed into the liquid reaction mixture with a small amount of water and the reaction mixture post stirred at 15° C. for 30 minutes. 125.5 grams of water (including the amount of rinse water) was added tot he reaction flask so that the theoretical percent solids in the aqueous phase was about 25 percent. The reaction mixture was agitated from 10 seconds to dissolve all solids before phase separation was performed.

The top organic phase (82.7 grams) was dried over 6.2 grams of magnesium sulfate to give a light yellow clear liquid (77.2 grams). Volatiles in the yellow liquid product were removed by a rotary evaporator under water aspirator vacuum (40 mm/Hg) for 60 minutes at 60° C., and then under vacuum pump (<2 mm/Hg) for 60 minutes at 60° C., thereby to obtain a final liquid product (71.8 grams). This product was a clear, light yellow liquid having an APHA color of 100. The conversion of chloroformate to chloride anion (Cl−) was found to be 100 percent based on the analysis for (Cl−) in the aqueous phase. The infrared spectrum of the product matched the literature infrared spectrum for diethyl pyrocarbonate with a characteristic band at 1823 cm−1. Both 1H (proton) and 13C nuclear magnetic resonance analysis supported the product as being diethyl pyrocarbonate with a minor amount of diethyl carbonate. The product has an assay of 96 percent as determined by gas chromatograph analysis.

EXAMPLE 2

The procedure of Example 1 was followed to synthesize diethyl pyrocarbonate, except that PEG-5 cocamine (0.85 grams, 0.002 mole) was used a the catalyst. The reaction gave a product of 95 percent assay in 82.4 percent yield. The final product was a colorless liquid having an APHA color of 15.

EXAMPLE 3

The procedure of Example 1 was followed except that the concentration of sodium hydroxide was varied from 7 percent to 50 percent. Results are tabulated in Table I.

TABLE I

| Run | % NaOH | % Chloroformate Conversion | % Purity | Color (APHA) | % Yield |
|---|---|---|---|---|---|
| 1 | 7 | 97 | 92 | 100 | 52 |
| 2 | 35 | 95 | 96 | 100 | 71 |
| 3 | 50 | 99 | 96 | 100 | 85 |

The data of Table I illustrate that the yield of diethyl pyrocarbonate increases with increasing concentration of sodium hydroxide.

COMPARATIVE EXAMPLE

Into a tared 500 ml four-necked reaction flask was added ethyl chloroformate (58.2 g, 0.525 mole, 99.1 percent assay), 42 ml of methylene chloride and 0.714 g (0.002 mole) of propoxylated N-methyl stearylamine catalyst. The catalyst, IMPRAFIX BU, was found to contain by analysis 1.26 moles of propylene oxide per mole of N-methyl stearylamine and had a molecular weight of 356.9. To the stirred reaction mixture was added dropwise sodium hydroxide (20.0 g, 0.50 mole) over one hour. The temperature of the reaction was maintained at 18°-20° C. by immersing a portion of the flask in an ice-water bath.

At the end of the addition of the sodium hydroxide, stirring was discontinued and two colorless phases formed almost immediately. The reaction mixture was stirred for another 15 minutes to insure completion of the reaction. Analysis of an aliquot of the aqueous phase for Cl− showed that the reaction product was 98 percent of theoretical.

The reaction mixture was phase separated in a 500 ml separtory funnel, and the aqueous phase extracted with 50 ml of methylene chloride. A considerable amount of cruddy, white interface was present. This emulsion was broken by passing it through glass wool in a gravity funnel.

The methylene chloride solution was dried overnight with anhydrous sodium sulfate. The solution was decanted, the sodium sulfate extracted twice with 25 ml portions of methylene chloride, decanted and the methylene chloride solutions combined. The colorless methylene chloride solution was distilled from a 100 ml three-necked flask through a 4-inch Vigreux-type Claisen adapter. Methylene chloride wad removed at atmospheric pressure by heating in a stirred 60°-63° C. oil bath. Additional methylene chloride, unreacted ethyl chloroformate and diethyl carbonate were collected by reducing the pressure to 20 mm Hg while heating in a 60° C. oil bath. The pressure was reduced to 5 mm Hg and the oil bath temperature increased to 91°-102° C. Diethyl pyrocarbonate distilled off at 76° C. at 5.5 mm Hg as a colorless liquid. The yield of diethyl pyrocarbonate was found to be 84 percent based on GLC analysis of foreshots from the distillation.

Although the present invention has been described with reference to the specific details of particular embodiments thereof, it is not intended that such details be regarded as limitations upon the scope of the invention, except insofar as and to the extend that they are included in the accompanying claims.

What is claimed is:

1. In the process of preparing di(organo) esters of pyrocarbonic acid by reaction of the corresponding organohaloformate with aqueous solution of alkali metal hydroxide, the improvement which comprises conducting said reaction in the substantial absence of an organic solvent and in the presence of a catalytic amount of a bis[poly(oxy($C_2$-$C_4$)alkylene)] $C_6$-$C_{20}$ aliphatic amine.

2. The process of claim 1 wherein the di(organo) ester of pyrocarbonic acid is represented by the graphic formula, $$R-O-\overset{O}{\underset{\|}{C}}-O-\overset{O}{\underset{\|}{C}}-O-R'$$

wherein R and R' are each selected from the group consisting of $C_1$-$C_{12}$ alkyl, $C_6$-$C_{10}$ cycloalkyl and $C_6$-$C_9$ aryl.

3. The process of claim 1 wherein the bis[poly(oxyalkylene)] $C_6$-$C_{20}$ aliphatic amine is represented by the graphic formula, $$R_1-N\begin{matrix}-(C_nH_{2n}O)_xH \\ -(C_nH_{2n}O)_yH\end{matrix}$$

wherein $R_1$ is a $C_6$-$C_{20}$ alkenyl, n is an integer of from 2 to 4, and x and y are each average numbers of from about 2 to about 24, the sum of x and y being a number from about 4 to about 48.

4. The process of claim 3 wherein the di(organo) ester of pyrocarbonic acid is represented by the graphic formula, $$R-O-\overset{O}{\underset{\|}{C}}-O-\overset{O}{\underset{\|}{C}}-O-R$$

wherein R is selected from the group consisting of $C_1$-$C_{12}$ alkyl, $C_6$-$C_{10}$ cycloalkyl and $C_6$-$C_9$ aryl.

5. The process of claim 1 wherein the alkali metal hydroxide is sodium hydroxide.

6. The process of claim 4 wherein the alkali metal hydroxide is sodium hydroxide.

7. The process of claim 6 wherein the concentration of sodium hydroxide is from 35 to 50 percent.

8. The process of claim 1 wherein from 0.1 to 1.0 mole percent of the catalyst, based on the organohaloformate, is used.

9. In the process of preparing dialkyl esters of pyrocarbonic acid represented by the graphic formula, $$R-O-\overset{O}{\underset{\|}{C}}-O-\overset{O}{\underset{\|}{C}}-O-R'$$

wherein R and R' are each a $C_2$-$C_8$ alkyl, by reaction of the corresponding alkyl chloroformate with an aqueous sodium hydroxide solution, the improvement which comprises conducting said reaction in the substantial absence of an organic solvent and in the presence of a catalytic amount of a bis[poly(oxy($C_2$-$C_4$)alkylene)] alkyl amine represented by the graphic formula, $$R_1-N\begin{matrix}-(C_nH_{2n}O)_xH \\ -(C_nH_{2n}O)_yH\end{matrix}$$

wherein $R_1$ is a $C_8$-$C_{18}$ alkyl, n is an integer of from 2 or 3, and x and y are each average numbers of from about 2 to about 14, the sum of x and y being a number of from 4 to 28.

10. The process of claim 9 wherein R and R' are ethyl and n is 2.

11. The process of claim 9 wherein from 0.1 to about 1.0 mole percent of catalyst based on the chloroformate is used.

12. The process of claim 10 wherein from about 0.1 to about 1.0 mole percent of catalyst based on the chloroformate is used.

13. The process of claim 1 wherein the bis[poly(oxyalkylene)]$C_6$-$C_{20}$ aliphatic amine is represented by the graphic formula, $$R_1-N\begin{matrix}-(C_aH_{2a}O)_x(C_bH_{2b}O)_{x'}H \\ -(C_aH_{2a}O)_y(C_bH_{2b}O)_{y'}H\end{matrix}$$

wherein $R_1$ is a $C_6$-$C_{20}$ alkyl or $C_6$-$C_{20}$ alkenyl, a and b are different and are integers of from 2 to 4, x and y are each numbers averaging from 1 to 24, x' and y' are each numbers averaging from 0 to 23, the sum of x, x', y and y' being a number of from about 4 to about 48.

14. The process of claim 13 wherein the di(organo)ester of pyrocarbonic acid si represented by the graphic formula, $$R-O-\overset{O}{\underset{\|}{C}}-O-\overset{O}{\underset{\|}{C}}-O-R'$$

wherein R and R' are each selected from the group consisting of $C_1$-$C_{12}$ alkyl, $C_6$-$C_{10}$ cycloalkyl and $C_6$-$C_9$ aryl.

15. The process of claim 6 wherein the catalyst is selected from the group consisting of polyoxyethylene (5) cocamine and polyoxyethylene (15) octadecylamine.

16. The process of claim 11 wherein the catalyst is selected from the group consisting of polyoxyethylene (5) cocamine and polyoxyethylene (15) octadecylamine.

17. The process of claim 6 wherein from 0.1 to 1.0 mole percent of catalyst, based on the organohaloformate, is used.

18. The process of claim 17 wherein the mole ratio of alkali metal hydroxide to organohaloformate is from about 1.10:1 to 1:1.10.

19. The process of claim 12 wherein the mole ration of alkali metal hydroxide to alkyl chloroformate is from about 1.10:1 to 1:1.10.

20. The process of claim 19 wherein the catalyst is selected from the group consisting of polyoxyethylene (5) cocamine and polyoxyethylene (15) octadecylamine.

* * * * *

UNITED STATES PATENT AND TRADEMARK OFFICE
CERTIFICATE OF CORRECTION

PATENT NO. : 5,231,211
DATED : July 27, 1993
INVENTOR(S) : Robert H. Tang

It is certified that error appears in the above-indentified patent and that said Letters Patent is hereby corrected as shown below:

Column 7, claim 3, line 25, after "is a" add -- $C_6$-$C_{20}$ alkyl or--

Column 8, claim 9, line 9, "a bout" should be --about--.

Column 8, claim 12, line 17, "a bout" should be --about--.

Column 8, claim 14, line 34, "si" should be --is--.

Signed and Sealed this

Twenty-sixth Day of April, 1994

*Attest:*

BRUCE LEHMAN

*Attesting Officer*     *Commissioner of Patents and Trademarks*